(12) United States Patent
Kuo

(10) Patent No.: US 10,533,026 B2
(45) Date of Patent: Jan. 14, 2020

(54) SUPPORTED MOLYBDENUM PEROXO COMPLEXES FOR TRANSFORMING ORGANO PHOSPHATE NEUROTOXINS TO A VALUE-ADDED, COMMODITY PHOSPHORUS CHEMICAL

(71) Applicant: Lewis & Clark College, Portland, OR (US)

(72) Inventor: Louis Kuo, Portland, OR (US)

(73) Assignee: Lewis & Clark College, Portland, OR (US)

( * ) Notice: Subject to any disclaimer, the term of this patent is extended or adjusted under 35 U.S.C. 154(b) by 0 days.

(21) Appl. No.: 15/937,672

(22) Filed: Mar. 27, 2018

(65) Prior Publication Data

US 2018/0282354 A1  Oct. 4, 2018

Related U.S. Application Data

(60) Provisional application No. 62/479,904, filed on Mar. 31, 2017.

(51) Int. Cl.
*B01J 31/16* (2006.01)
*C07F 9/142* (2006.01)
*C07F 9/40* (2006.01)

(52) U.S. Cl.
CPC .......... *C07F 9/4021* (2013.01); *B01J 31/165* (2013.01); *C07F 9/142* (2013.01); *C07F 9/4075* (2013.01); *B01J 2531/64* (2013.01)

(58) Field of Classification Search
CPC combination set(s) only.
See application file for complete search history.

(56) References Cited

U.S. PATENT DOCUMENTS 9,024,106 B2 * 5/2015 Kuo .................... A62D 3/38
588/401

OTHER PUBLICATIONS

Kurusu et al. J. Molec. Catal. 1986, 37, 235-241. (Year: 1986).*
Blasko et al., "Oxidative Hydrolysis of Phoshorus(V) Esters of Thiols by Peroxymonosulfate Ion, Reactions of Peroxymonosulfate Ion with Phosphorus(V) Esters of Thiols", Journal of Physical Organic Chemistry, vol. 10, pp. 427-434, Jan. 22, 1997.
Boruah et al., "Polymer-Anchored Peroxo Compounds of Vanadium(V) and Molybdenum(VI): Synthesis, Stability, and Their Activities with Alkaline Phosphatase and Catalase", Inorganic Chemistry, vol. 50, pp. 8046-8062, 2011.
Chanda et al., "Total Degradation of Fenitrothion and Other Organophosphorus Pesticides by Catalytic Oxidation Employing Fe-TAML Peroxide Activators", Journal American Chemical Society, vol. 128, pp. 12058-12059, Jun. 7, 2006.
El-Amamy et al., "Hydrolysis Kinetics of Organic Chemicals on Montmorillonite and Kaolinite Surfaces as Related to Moisture Content", Clays and Clay Minerals, vol. 32, No. 1, pp. 67-73, 1984.
Hendry et al., "Base Hydrolysis of Coordinated Trimethyl Phosphate", Australian Journal of Chemistry, vol. 39, pp. 1177-1186, 1986.
Jia et al., "Mesoporous MCM-41 Materials Modified with Oxodiperoxo Molybdenum Complexes: Efficient Catalysts for the Epoxidation of Cyclooctene", Chem. Mater., vol. 15, pp. 2174-2180, Feb. 10, 2003.
Jokanovic et al., "Neurotoxic effects in patients poisoned with organophosphorus pesticides", Environmental Toxicology and Pharmacology, vol. 29, pp. 195-201, Feb. 2, 2010.
Klabunde, Kenneth, "Multifunctional nanostructured catalysts and sorbents: Destructive adsorbents enhanced by solar energy or photochemical boosting", Main Group Chemistry 9, vol. 9, pp. 297-307, 2010.
Kuo et al., "Heterogeneous Organophosphate Ethanolysis: Degradation of Phosphonothioate Neurotoxin by a Supported Molybdenum Peroxo Polymer", Inorganic Chemistry, vol. 56, pp. 10013-10020, Aug. 2, 2017.
Kurusu et al., "Epoxidation with t-BUTYL Hydroperoxide in the Presence of Molybdenum Peroxide and Polymer-Immobilized Molybdenum Peroxide", Journal of Molecular Catalysis, vol. 37, pp. 235-241, May 2, 1986.
Marciano et al., "Catalytic Degradation of the Nerve Agent VX by Water-Swelled Polystyrene-Supported Ammonium Fluorides", Journal of Organic Chemistry, vol. 76, pp. 8549-8553, Sep. 11, 2011.
"Parathion", https://www.epa.gov/sites/production/files/2016-09/documents/parathion.pdf, 4 pages, accessed on Aug. 21, 2018.
"Parathion—toxicity, ecological toxicity and regulatory information", http://www.pesticideinfo.org/Detail_Chemica.jsp?Rec_ID=PRI4784, 8 pages, accessed on Apr. 8, 2019.
Rauch et al., "Associations of Prenatal Exposure to Organophosphate Pesticide Metabolites with Gestational Age and Birth Weight", Environmental Health Perspectives, vol. 120, pp. 1055-1060, Jul. 2012.
Rauh et al., "Brain anomalies in children exposed prenatally to a common organophosphate pesticide", PNAS, vol. 109, No. 20, pp. 7871-7876, May 15, 2012.
Saltzman et al., "Role of Water in the Hydrolysis of Parathion and Methylparathion on Kaolinite", J. Agric. Food Chem., vol. 24, No. 24, pp. 739-743 1976.
Seger et al., "NMR Investigation of the Behavior of an Organothiophosphate Pesticide, Methyl Parathion, Sorbed on Clays", Environ. Sci. Technol., vol. 40, pp. 552-558, 2006.
Torrents et al., "Oxide Surface-Catalyzed Hydrolysis of Carboxylate Esters and Phosphorothioate Esters", Soil Sci. Soc. Am. J., vol. 58, pp. 738-745, 1994.
Wan et al., "Mercury(II) Ion-Promoted Hydrolysis of Some Organophosphorus Pesticides", Pestic. Sci., vol. 42, pp. 93-99, Jun. 20, 1994.
Wu et al., "Oxidatively-Induced Formation of Dialkyl Hydrogenphosphonates From Phosphorothionates", Phosphorus, Sulfur, and Silicon, vol. 54, pp. 221-224, 1990.

* cited by examiner

*Primary Examiner* — Amanda L Aguirre
(74) *Attorney, Agent, or Firm* — McKee, Voorhees & Sease, PLC

(57) ABSTRACT

The invention relates to degradation of organophosphate neurotoxins with molybdenum complexes. In particular, the degradation of phosphate ester neurotoxins can be performed with molybdenum peroxo complexes resulting in recoverable phosphorus-containing compounds.

19 Claims, 6 Drawing Sheets

SUPPORTED MOLYBDENUM PEROXO COMPLEXES FOR TRANSFORMING ORGANO PHOSPHATE NEUROTOXINS TO A VALUE-ADDED, COMMODITY PHOSPHORUS CHEMICAL

CROSS-REFERENCE TO RELATED APPLICATION

This is related to and claims priority under 35 U.S.C. § 119 to U.S. Provisional Ser. No. 62/479,904, filed Mar. 31, 2017, which is herein incorporated by reference in its entirety, including but not limited to, the description, figures, tables, claims, and appendix.

GRANT REFERENCE

This invention was made with government support under the National Science Foundation, contract Grant No. CHE-1413090. The Government has certain rights in this invention.

FIELD OF THE INVENTION

The invention relates to degradation of organophosphate neurotoxins with molybdenum complexes. In particular, the degradation of phosphate ester neurotoxins can be performed with molybdenum peroxo complexes resulting in recoverable phosphorus-containing compounds.

BACKGROUND

Phosphate esters are a class of chemicals that includes numerous chemical warfare agents such as VX, pesticides, and insecticides, further including paraoxon and parathion. Each of these compounds includes a phosphate ester bond, and irreversibly blocks a serine hydroxyl group within the enzyme acetylcholinesterase by phosphorylation, resulting in a disruption of a cell's neurologic function. Thus, many organophosphate compounds can be neurotoxic. Further, phosphate esters used as pesticides can be toxic to animals and also pollute soil and water. The creation of phosphate esters for chemical warfare and use as pesticides results in the need for a safe and effective process of degradation in order to completely eliminate the compounds without persistent toxic environmental and medical effects. Thus, it has been desirable to find methods of degrading organophosphate compounds. Much of the work in finding suitable methods for degrading phosphate esters in pesticides originates from the research done to degrade phosphate ester nerve agents.

Sulfur-containing containing organophosphates are used as systemic neurotoxins for agricultural and residential pesticides. For example, diazonin (thiophosphate) was used widely in the United States as an insecticide against cockroaches, silverfish, ants and fleas. It is also used to control pest insets in soil, on plants and on fruit and vegetable field crops. Prior to a residential ban (2004) on residential use, diazonin was heavily used and it was estimated up to 80% of all residential lawn and garden insecticides contained diazonin (13 million pounds/year). 10 Due to its heavy use, diazonin is prevalent in the environment. The US Geological Survey National Stream Water Quality Network found diazonin in all major U.S. river systems including the Rio Grande, Mississippi, Columbia and Colorado at levels exceeding the safety limit for aquatic organisms.

Like all organophosphates, diazonin is an acetylcholine esterase inhibitor that acts as a neurotoxin. In humans diazonin overstimulates the nervous system that may result in nausea, dizziness and confusion, and high levels it can cause respiratory weakness, headaches and death. Diazonin is listed as a developmental toxin in the EPA's Toxics Release Inventory. Another similar thiophosphate pesticide is parathion which is still in agricultural use. The US EPA considers parathion as a possible human carcinogen 12 and the non-governmental organization Pesticide Action Network (PAN) considers parathion as one of the most dangerous pesticides. It was used as a chemical warfare weapon by the Selous Scouts during Rhodesian Bush War (1964-1979). The WHO and PAN propose a general and global ban on parathion; its use is banned and restructured in 23 countries and its import is illegal in 50 countries. Methyl parathion is approved for use as an agricultural pesticide but in 1999 the EPA canceled its use on food crops consumed by children such as apples, peaches, pear, carrots and peas. It is allowed in other crops such as vegetables, nuts and grains that may be eaten by humans.

In addition to targeting the pesticides, there is a need to degrade military organophosphate neurotoxins. O-ethyl-S-[2-diisopropylamino)ethyl]methylphosphonothioate (commonly referred to as VX) is such a chemical warfare agent. Symptoms of exposure to VX include coughing, difficulty breathing, sweating, vomiting, urination/defecation, headache, tremors, unsteadiness and confusion, ultimately progressing to death. It is the most lethal human-made neurotoxin. The United States has a stockpile of thousands of tons of VX that must be destroyed to comply with the Chemical Weapons Treaty of 1997. In addition, Russia is also known to possess quantities of VX.

Traditionally, VX is degraded on a large scale by hydrolysis with concentrated aqueous sodium hydroxide resulting in competing cleavage of the P—S and P—O esters, with approximately 87% P—S bond cleavage and 13% P—O bond cleavage. This is problematic because the byproduct of the P—O bond cleavage, S-[2-(diisopropylamino)ethyl] methylphosphonic acid, has a toxicity comparable to VX and requires additional steps such as oxidative pretreatment for destruction. Caustic neutralization at 90° C. (16.6 wt. % VX, 8.8 wt. % NaOH, 74.6 wt. % $H_2O$) produces a similar ratio of bond cleavage, but allows S-[2-(diisopropylamino) ethyl]methyl-phosphonic acid to be broken down concurrently producing methyl phosphonic acid and thiolamine. However, this process requires specific control over both the pH and temperature of the reaction to ensure no byproducts are produced.

There is a need for a method to selectively cleave the P—S bond of the phosphate ester VX to eliminate the toxic byproducts of its degradation, so as not to require further degradation. Various additional aqueous compounds have been used in the degradation of VX, but are either unsuccessful at selectively cleaving the P—S bond or present commercial difficulties in their ability to be used in mass quantities. For example, aqueous potassium peroxymonosulfate selectively cleaves the P—S bond in VX. However, the solubility of potassium peroxymonosulfate is limited at low pH and the oxidant decomposes at any pH above 5. Alternatively, the use of potassium peroxymonosulfate in polar organic solvents generates a toxic diphosphonate as a major byproduct.

Other degradation methods for phosphonothioates include incineration and oxidation with peroxides. Incineration is a politically unacceptable degradation method which is no longer actively pursued by the United States. Alternatively, hydrolytic degradation of phosphonothioates lacks selectivity and results in both P—O and P—S degradation pathways, resulting in toxic byproducts.

The known methods to degrade phosphate ester pesticides include hydrolysis by microorganisms, degradation or hydrolysis by Cu (II), Hg(II) and clays, surface catalyzed hydrolysis by $Al_2O_3$, $TiO_2$ and FeOOH (goethite), and hydrolysis by Rh(III) and Ir(III) coordination complexes that are overly expensive.

Still another method of degrading phosphate esters includes a heterogeneous-phase method that targets organophosphates in a passive approach binding or sequestering the neurotoxins. One of the more convenient approaches to this is with smetic clay that can actively degrade these phosphate ester pesticides. However, degradation by smetic clay takes up to one year.

Therefore, an immediate problem that must be addressed is a convenient and benign way to degrade these ubiquitous organophosphate pesticides and chemical warfare agents. Moreover, the method and material has to be easily made, stable in most environmental conditions, facilely recycled and target against a general array of sulfur-containing organophosphate pesticides.

There is also a need to recycle the organophosphate product for phosphorus recovery, which has been identified as a national priority by the National Science Foundation. The United States and China have an estimated 30-year domestic supply of minable phosphorus. Therefore, by the middle of this century the world's two largest economies may run out of affordable supplies of domestic phosphorus. Europe has labeled phosphorus as a "critical material," and it will soon compete with the U.S. and China for the dwindling phosphorus supply. The need for phosphorus recovery is best summarized by a quote from Isaac Asimov where he said "life can multiply until all phosphorus is gone, and then there is an inexorable halt which nothing can prevent. . . . We may be able to substitute nuclear power for coal, and plastics for wood, and yeast for meat . . . but for phosphorus there is neither substitute nor replacement."

Prior heterogeneous-phase methods that target organophosphates take a passive approach that bind or sequester the neurotoxins; perhaps the most convenient material is smetic clay that actively degrades these pesticides. However, degradation by smetic clay takes up to one year. The supported molybdenum polymers of this invention effectively degrade these pesticides in a period of days. Moreover, in this invention the active species is regenerated with the addition of $H_2O_2$ and is catalytic in the molybdenum metal immobilized on the support. A prior example using a polystyrene ammonium fluoride successfully degrades VX but in a non-catalytic fashion and goes through a toxic phospho fluoridate (i.e., Sarin) intermediate.

Additionally, the prior methods of degrading organophosphate compounds has not provided the ability to recover useful chemicals (such as phosphorus) from the degradation process. Rather the approach has focused on degrading the compounds such that they are capable of disposal.

Thus, there is a need for new methods of degrading organophosphate compounds. Further, there is a need for degradation methods that can result in the recovery of useful chemicals, such as phosphorus.

Accordingly, it is an objective of the claimed invention to develop

A further object of the invention is to provide a method of degrading phosphate esters in a shorter time period and under more mild conditions.

Still a further object of the invention is to provide a method of degrading phosphate esters that can result in the recovery of useful phosphorus-containing compounds.

Other objects, advantages and features of the present invention will become apparent from the following specification taken in conjunction with the accompanying figures.

Figure 1:
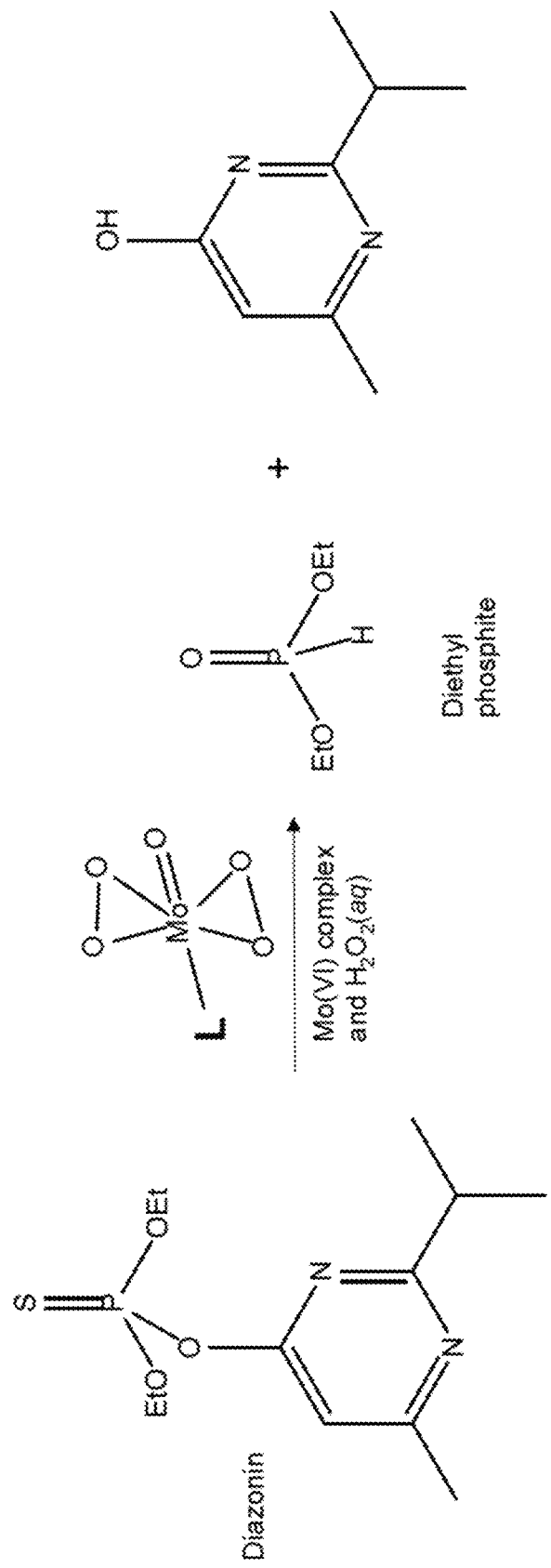
FIG. 1 shows an exemplary molybdenum(VI) complex driven degradation reaction of diazonin. The reaction products comprise diethyl phosphite, a phosphorus compound having commercial value.

Various embodiments of the present invention are described in detail with reference to the figures. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to molybdenum complexes and use of the same to degrade phosphate esters. The molybdenum complexes and degradation methods have many advantages over existing methods of degrading phosphate esters. For example, the active molybdenum species is immobilized and the separation of the degradation product is facile. Further, as a supported material, the active species can be regenerated with the addition of hydrogen peroxide. Another advantage is that the degradation can occur under mild conditions in a water or alcohol solvent and can result in safe byproducts.

It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

References to elements herein are intended to encompass any or all of their oxidative states and isotopes, unless otherwise specified. For example, discussion of phosphorus can include $P^{-3}$, $P^{-2}$, $P^{-1}$, $P^{+1}$, $P^{+2}$, $P^{+3}$, $P^{+4}$, and/or $P^{+5}$.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the term "analog" means a molecular derivative of a molecule. The term is synonymous with the terms "structural analog" or "chemical analog."

As used herein, the term "oligomer" refers to a molecular complex comprised of between one and ten monomeric units. For example, dimers, trimers, and tetramers, are considered oligomers. Furthermore, unless otherwise specifically limited, the term "oligomer" shall include all possible isomeric configurations of the molecule, including, but are not limited to isotactic, syndiotactic and random symmetries, and combinations thereof. Furthermore, unless otherwise specifically limited, the term "oligomer" shall include all possible geometrical configurations of the molecule.

As used herein the term "polymer" refers to a molecular complex comprised of a more than ten monomeric units and generally includes, but is not limited to, homopolymers, copolymers, such as for example, block, graft, random and alternating copolymers, terpolymers, and higher "x"mers, further including their analogs, derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "weight percent," "wt. %," "wt-%," "percent by weight," "% by weight," and variations thereof, as used herein, refer to the concentration of a substance as the weight of that substance divided by the total weight of the composition and multiplied by 100.

The terms "water soluble" and "water dispersible" as used herein, means that the polymer is soluble or dispersible in water in the inventive compositions. In general, the polymer should be soluble or dispersible at 25° C. at a concentration of 0.0001% by weight of the water solution and/or water carrier, preferably at 0.001%, more preferably at 0.01% and most preferably at 0.1%.

The methods and systems of the present invention may comprise, consist essentially of, or consist of the components and ingredients of the present invention as well as other ingredients described herein. As used herein, "consisting essentially of" means that the methods and systems may include additional steps, components or ingredients, but only if the additional steps, components or ingredients do not materially alter the basic and novel characteristics of the claimed methods, systems, apparatuses, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Degrading Phosphate Esters with Molybdenum(VI) Complexes

According to the invention, molybdenum (VI) complexes can be used in systems and methods for degrading phosphate esters. The systems and methods for degrading phosphate esters, can further comprise water, a polar solvent such as an alcohol, or a combination thereof.

Molybdenum (VI) Complexes

The Mo(VI)-oxoperoxo complexes comprise one or more monomers of the following formula:

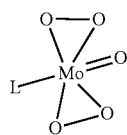

wherein L comprises a carbon-based support. The carbon-based support can comprise an oligomer and/or polymer. Preferably, the carbon support comprises a polyacrylate, polystyrene, or mesoporous silica. Preferably, the molybdenum(VI) oxoperoxo complex is immobilized on the carbon-based support.

Suitable polyacrylates include, but are not limited to, acrylate, methacrylate, or acrylamide monomers repeated between 10 and 10,000 times. Preferred polymers comprising acrylate, methacrylate, and/or acrylamide monomers have a molecular weight, calculated by the gel permeation chromatography method, between about 1000 and about 4000, more preferably between about 1500 and about 3500. The following are exemplary polyacrylates shown with the molybdenum complex bound:

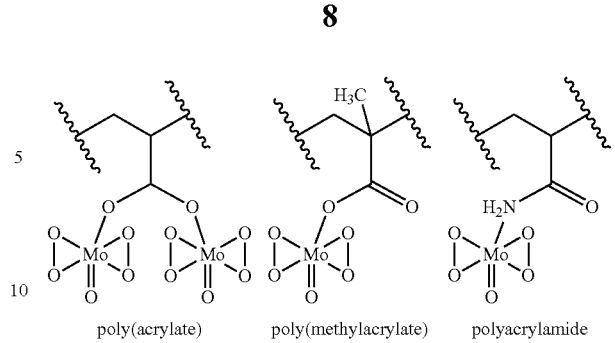

poly(acrylate)   poly(methylacrylate)   polyacrylamide

Suitable polystyrenes include, but are not limited to, the following:

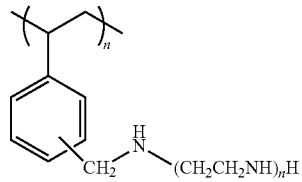

wherein n is between 1 and 10,000. Preferred polystyrenes have a molecular weight, calculated by the gel permeation chromatography method, between about 10,000 and about 45,000, more preferably between about 30,000 and about 40,000. The polystyrene binds to the molybdenum complex as shown below:

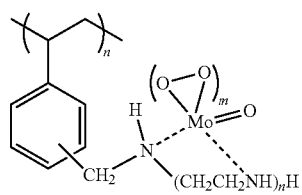

Suitable mesoporous silica, include, but are not limited to, Al-MSU—F, HMS, MCM-41, MSU—F, MSU—H, SBA-15, and combinations thereof. A preferred mesoporous silica comprises MCM-41 as shown in the following molybdenum (VI)

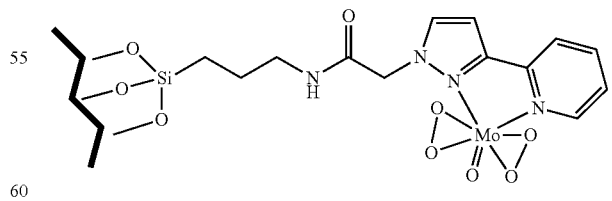

complex:

Phosphate Esters

According to an aspect of the invention, the systems and methods comprising molybdenum(VI) complexes can degrade phosphate esters.

Suitable phosphate esters for degradation according to the systems and methods of the invention include, but are not limited to, the following classes:

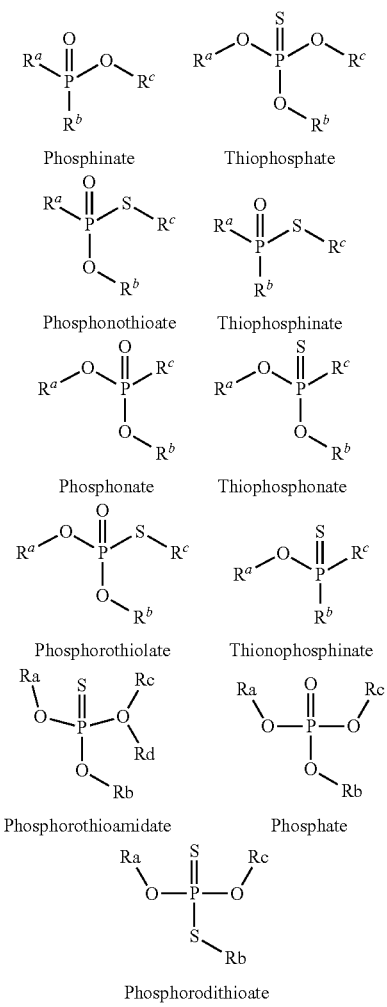

wherein $R^a$-$R^c$ are selected from the group consisting of hydrogen atoms, halides, R, OR, OCOR, SR, $NR_2$ and $PR_2$; and wherein R is selected from the group consisting of linear, branched, saturated and unsaturated $C_1$-$C_{20}$ alkyl, $C_3$-$C_{20}$ cycloalkyl, $C_6$-$C_{20}$ aryl, $C_7$-$C_{20}$ alkylaryl, $C_7$-$C_{20}$ arylalkyl radicals, optionally containing one heteroatom and multiple heteroatoms belonging to groups 13-17 of the Periodic Table. $R^a$-$R^c$ may also be joined to form five-member and six-member rings which include P.

Examples of suitable phosphate esters include, but are not limited to, Acephate, Azamethiphos, Azinphos-ethyl, Azinphos-methyl, Bromophos, Cadusaphos, Carbofuran, Carbophenothion, Chlorfenvinphos, Chloropyrifos, Chloropyrifos-methyl, Coumaphos, Crotoxyphos, Cyanophos, Cythioate, Demeton-O, DEPP, Diazinon, Dichlorofenthion, Dichlorvos, Dichrotophos, Dimethoate, Disulfoton, Echothiophate, Ethion, Famphur, Fenamiphos, Fenitrothion, Fenthion, Fonofos, Glyphosate, Gluphosinate ammonium, Glyphosine, Isazophos, Isofenphos, Malaoxon, Malathion, Methamidophos, Methidathion, Methyl parathion, Mevinphos, Monocrotophos, Naled, Naphthalophos, Omethoate, Oxydemeton-methyl, Parathion, Parathion-methyl, Paraoxon-methyl, Phenthoate, Phorate, Phosalone, Phosmet, Phosphamidon, Phosphonate Glyphosate, Phoxim, Pirimiphos-methyl, Profenofos, Propetamphos, Prothiofos, Quinalphos, Ronnel, Sulfotep, Sulfoprofos, Temephos, Terbufos, Tetrachlorinophos, Thiometon, Triazophos, Trichlorfon, and combinations, mixtures, derivatives, and/or precursors thereof.

Preferred phosphate esters can comprise a P=S functional group (such as parathion, diazaonin, and malathion), and O,S-diethylmethylphosphonothioate (DEPP). Thus in an aspect of the invention, preferred phosphate esters for degradation include, but are not limited to, parathion, diazonin, O,S-diethylmethylphosphonothioate (DEPP), and malathion.

Peroxygen Source

The systems and methods can comprise a peroxygen source. Preferred peroxygen sources include, but are not limited to, hydrogen peroxide, t-butyl peroxide, or a mixture thereof. In an aspect of the invention, the peroxygen source can be added in excess of the other components in the reaction. In some embodiments of the invention the ratio of peroxygen source to phosphate ester is at least about 2:1, preferably about 4:1, more preferably at least about 7:1, most preferably at least about 10:1. In some embodiments of the invention the ratio of peroxygen source to molybdenum (VI) complex is at least about 2:1, preferably about 4:1, more preferably at least about 7:1, most preferably at least about 10:1.

Water and/or Polar Solvent

The system and methods can comprise water, polar solvent, or combination thereof as a medium for the degradation reaction. Preferred polar solvents include water soluble solvents. Preferred polar solvents include, but are not limited to, alkyl chain alcohols having between 1 and 10 carbons in the alkyl group, acetonitrile, and the like. Methanol, butanol, ethanol, acetonitrile and mixtures thereof are most preferred polar solvents.

Beneficially, molybdate and molybdenum organometallics are soluble in water. Preferably, if using a polar solvent, instead of water, the polar solvent chosen is one that molybdate and molybdenum organometallics are soluble in.

The medium for the degradation reaction can be mixture of water and a polar solvent. In some embodiments of the invention, water can be between about 0.01 vol. % and about 100 vol. % of the reaction medium. In some embodiments of the invention, a polar solvent or mixture of polar solvents can be between about 0.01 vol. % and about 100 vol. % of the reaction medium. In a preferred embodiment of the invention, the reaction medium is water or a 50:50 mixture by volume of water and a polar solvent.

Additional Components

The reaction vessel can further comprise additional components that may be useful in the degradation reaction or to control the formation of reaction products. For example, acetonitrile can be added to the reaction vessel. Reaction catalysts and/or pH modification agents can also be added to the reaction vessel. In some embodiments, no additional components are added.

System

The systems of the invention can comprise a reaction vessel. The reaction vessel can comprise an inlet and/or an outlet. The reaction vessel can comprise more than one inlet and more than one outlet. In a preferred embodiment, the reaction vessel can include an inlet for the various components added to the reaction vessel; for example, an inlet for the phosphate ester, an inlet for the hydrogen peroxide, an inlet for the water and/or polar solvent, and an inlet for the molybdenum(VI) complex. However, in some embodiments, one or more of the components can use the same inlet. In embodiments of the invention, the reaction vessel can comprise one or more outlets. In a preferred embodiment, one or more reaction products can pass through one or more outlets.

The systems of the invention can comprise one or more recovery apparatuses to recover one or more reaction products. Preferably, the recovery apparatus is in fluid communication with the reaction vessel. In a preferred embodiment of the invention, the reaction product comprises a phosphorus-containing compound derived from a degraded phosphate ester. In some embodiments of the invention, the reaction product can comprise diethyl phosphite or diethyl phenylphosphonate.

The systems of the invention can comprise a temperature control. Any suitable temperature control can be employed. Preferably the temperature of the reaction vessel is between about 10° C. and about 50° C., more preferably between about 20° C. and about 45° C., most preferably between about 30° C. and about 40° C.

The systems of the invention can include one or more pumps to control the flow of various components into and out of the reaction vessel. In an aspect of the invention, the pumps can control the amount of components added to the reaction vessel so as to maintain a desired ratio of components for the degradation reaction to occur.

Preparation of Mo(VI) Complexes

Preparation of the molybdenum(VI) complexes. The molybdenum(VI) oxoperoxo complexes can be prepared according to any suitable method, which can be specific to the carbon-based support. Preferably, the molybdenum(VI) complex is prepared by mixing molybdenum with a peroxygen source (preferably hydrogen peroxide) and allowing the two to react. Preferably, the mixture of molybdenum and peroxygen source can be stirred. After reacting, a carbon-based support (e.g., a polyacrylate, a polystyrene, or a mesoporous silica) can be added to the mixture. Preferably the mixture of molybdenum, peroxygen source, and carbon-based support are stirred. The resultant complex can be filtered and washed.

A preferred method of preparing a Mo(VI) oxoperoxo complex with a polystyrene is that described by Kurusu et al., "Epoxidation with t-butyl hydroperoxide in the presence of molybdenum peroxide and polymer-immobilized molybdenum peroxide," *J. Molec. Cat.* 1986, 37 (2), 235-242.

Degradation of Phosphate Esters

In an aspect of the invention, the phosphate ester(s) can be degraded in a heterogenous reaction with the molybdenum (VI) oxoperoxo complexes. In an aspect of the invention, the reaction products can be separated from the active species, which remains in solid phase. Moreover, the reaction products can include commercially valuable phosphorus-containing products. Further, in preferred embodiments, the reaction can occur in an environmentally benign manner. Additionally, the degradation can be completed in a time between 6 hours and 10 days, preferably between 12 hours and 7 days, more preferably between 1 day and 5 days.

In embodiments of the invention, the molybdenum(VI) complexes can selectively cleave the P—S bond so that toxic by-products are avoided. This is an improvement over existing degradation methods that could not select between P—O bonds and P—S bonds. Thus, the selective P—S bond scission of the invention provides a significant benefit over existing degradation methods. Further, in certain embodiments, the reaction products can include diethyl phosphite, which is a valuable phosphorus-containing chemical.

Figure 2:
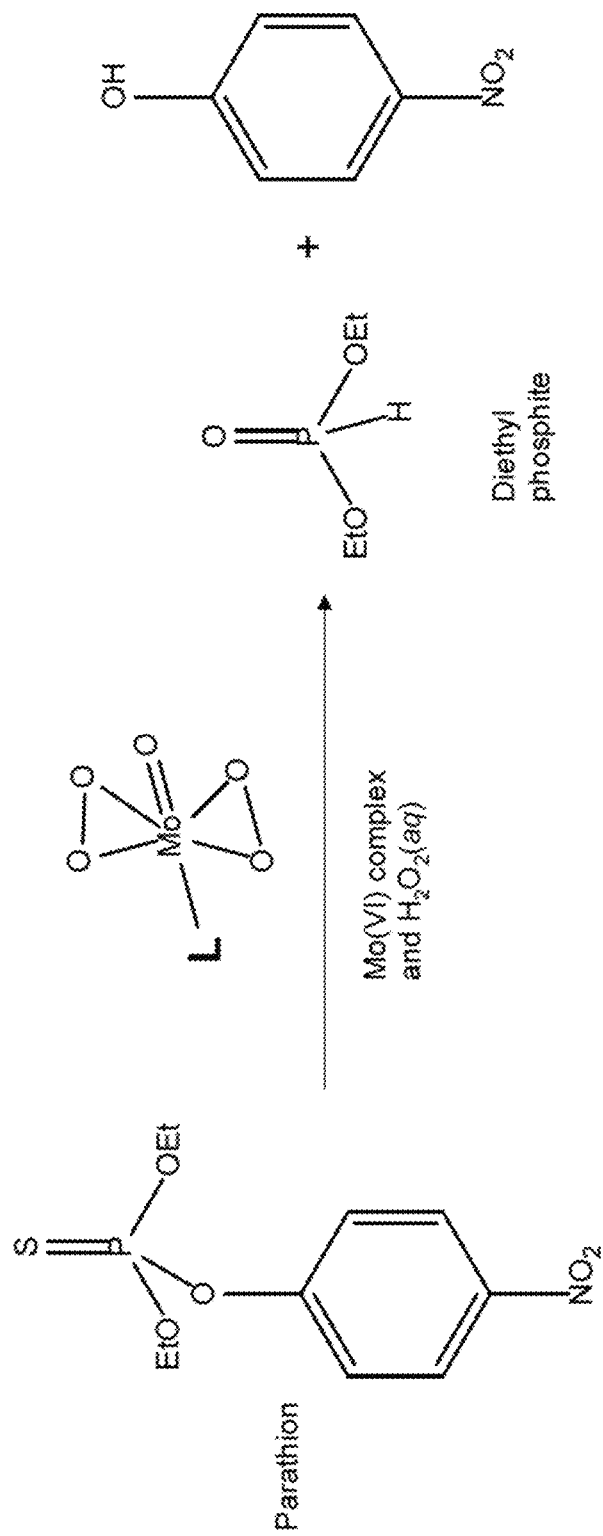
FIG. 2 shows an exemplary molybdenum(VI) complex driven degradation reaction of parathion. The reaction products comprise diethyl phosphite, a phosphorus compound having commercial value.
Figure 3:
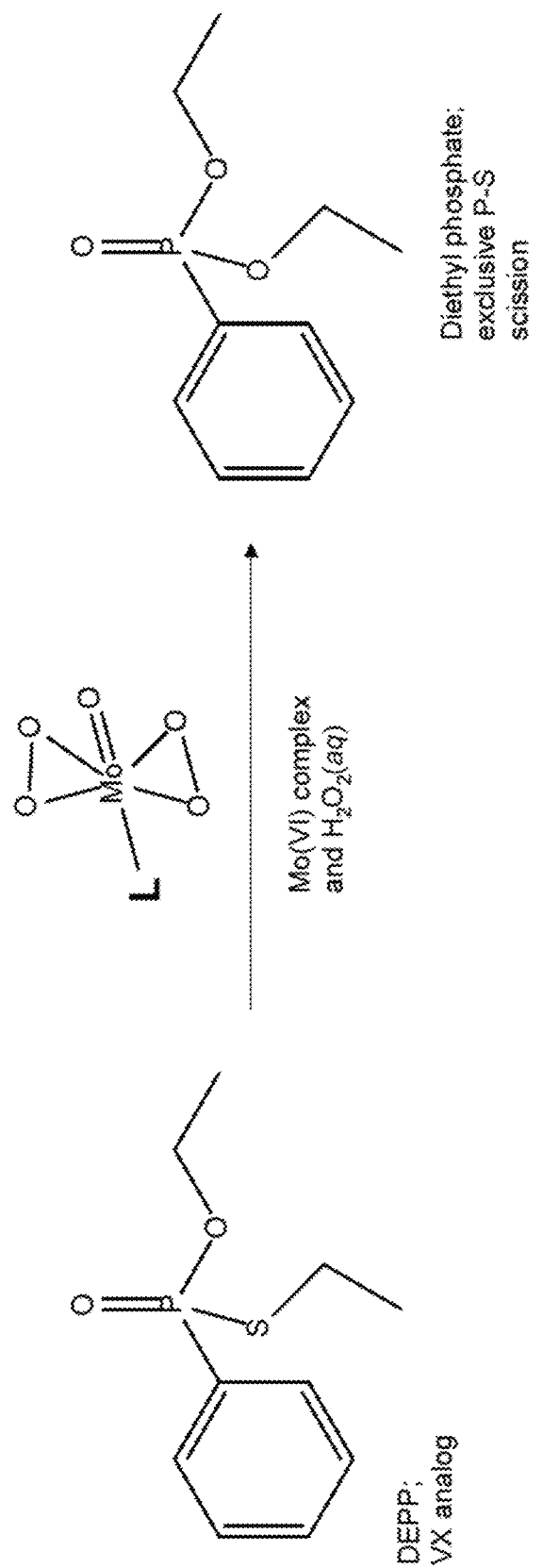
FIG. 3 shows an exemplary molybdenum(VI) complex driven degradation reaction of O,S-diethylmethylphosphonothioate (DEPP). This exemplary degradation demonstrates a selective P—S bond scission.

Exemplary degradation reactions and their reaction products are demonstrated in FIGS. 1-3. FIG. 1 shows an exemplary molybdenum(VI) complex driven degradation reaction of diazonin. FIG. 2 shows an exemplary molybdenum(VI) complex driven degradation reaction of parathion. The reaction products of both degradation reactions of in FIGS. 1-2 include diethyl phosphite. FIG. 3 shows an exemplary molybdenum(VI) complex driven degradation reaction of O,S-diethylmethylphosphonothioate (DEPP). This exemplary degradation demonstrates a selective P—S bond scission.

In some embodiments of the invention, the degradation reaction can comprise an alcoholysis reaction, preferably an ethanolysis reaction. Further, in some embodiments of the invention, the degradation reaction can comprise a selective P—S bond scission. In a preferred embodiment, the degradation reaction does not include a P—O bond scission.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Degradation of Diazonin

A molybdenum(VI) polystyrene complex were prepared by adding 10 mL of 30% aqueous $H_2O_2$ to 0.75 grams of molybdenum(VI) powder over a two-minute time period at room temperature in a wide-mouth beaker. The suspension was allowed to stir for 4.5 minutes where upon it changes from green to a bright yellow color.

To the yellow suspension, 2.1 grams of a polystyrene polymer (Diaion CR20 polymer available from Mitsubishi Chemical Co.) was added over a span of 2.5 minutes. The yellow suspension-beads were slowly stirred (to avoid damaging the beads) at room temperature for 18 hours. The beads were filtered on a fritted funnel, washed with distilled water (100 mL) followed by a 100-mL wash with diethyl ether.

Figure 4:
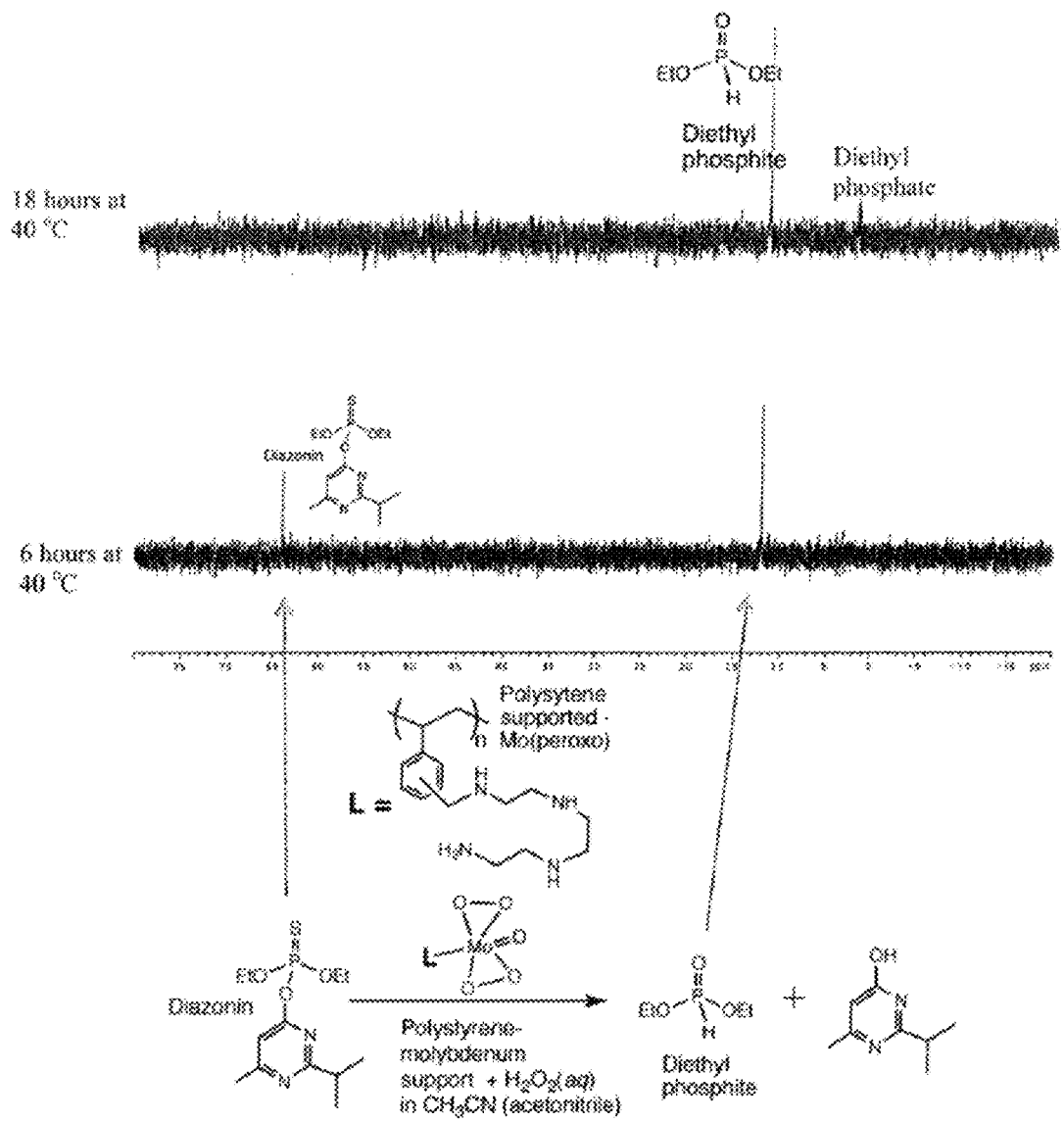
FIG. 4 is a phosphorus-31 nuclear magnetic resonance (NMR) spectra of the degradation of diazonin according to an embodiment of the invention at 6 hours and 18 hours.

In a typical degradation reaction, 1.0 mL of acetonitrile was added to 100 mg of the polystyrene-supported molybdenum-peroxo compound. This was followed by 15 µL 30% aqueous $H_2O_2$ or t-butyl peroxide and the suspension was allowed to sit for 30 minutes until the mild bubbling ceased. After the 30-minute wait, the organophosphate neurotoxin was added and monitored with nuclear magnetic resonance (NMR) spectroscopy. The results of the NMR are shown in FIG. 4.

As shown from the two phosphorus-31 NMR spectra (FIG. 4), there is exclusive formation of only one product after 18 hours; this product was identified as the commodity chemical diethyl phosphite through authentic addition. At 6 hours a peak at ~65 ppm representing diazonin was clearly visible. After only 18 hours at 40° C. the starting phosphorus-31 signal (singlet at ~65 ppm) representing diazonin is completely gone and predominantly one product is produced (i.e., diethyl phosphite at 12 ppm).

Example 2

Degradation of Parathion

A molybdenum(VI) complex with a polystyrene carbon-based support was prepared as described in Example 1.

Figure 5:
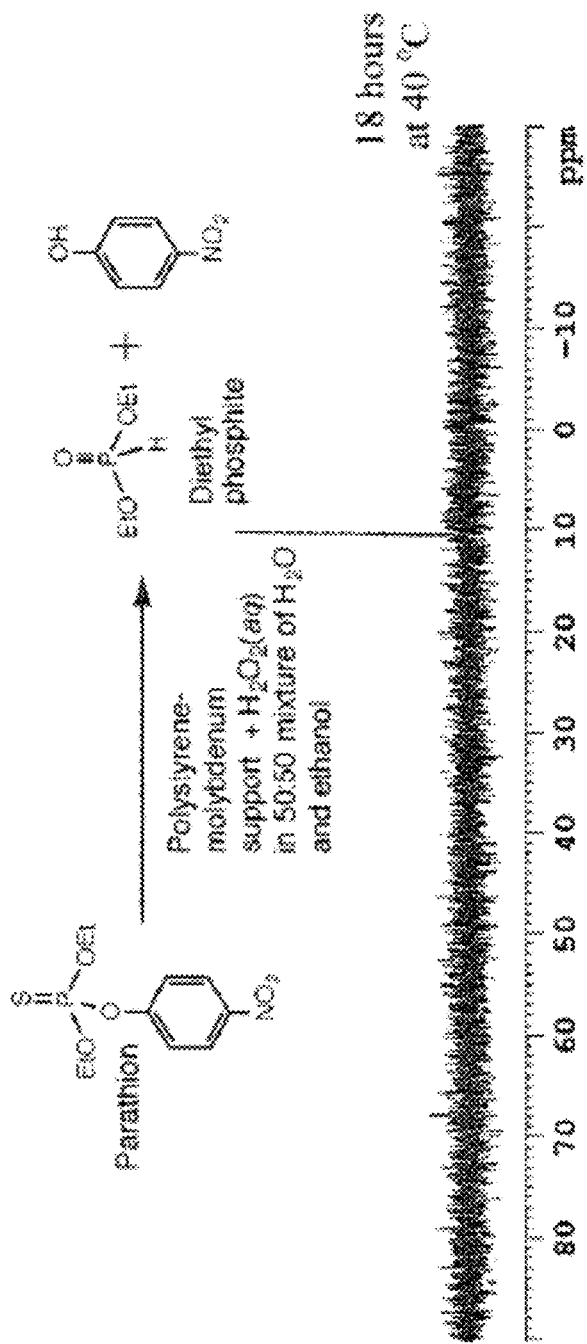
FIG. 5 is a phosphorus-31 NMR spectra of the degradation of parathion according to an embodiment of the invention at 18 hours.

30% aqueous $H_2O_2$ or t-butyl peroxide was added to the suspension and allowed to sit for 30 minutes until the mild bubbling ceased. After the 30-minute wait, the organophosphate neurotoxin parathion was added and monitored with nuclear magnetic resonance (NMR) spectroscopy. A 50:50 mixture of water and ethanol served as the reaction medium. The NMR spectra measured at 18 hours are shown in FIG. 5.

As shown from the phosphorus-31 NMR spectra (FIG. 5), there is exclusive formation of only one product after 18 hours; this product was identified as the commodity chemical diethyl phosphite (peak at ~11 ppm) through authentic addition.

Example 3

Degradation of DEPP

A molybdenum(VI) complex with a polystyrene carbon-based support was prepared as described in Example 1.

30% aqueous $H_2O_2$ or t-butyl peroxide was added to the suspension and allowed to sit for 30 minutes until the mild bubbling ceased. After the 30-minute wait, the organophosphate neurotoxin DEPP was added and monitored with phosphorus-31 NMR spectroscopy. A 50:50 mixture of water and ethanol served as the reaction medium. The NMR spectra measured at 0, 0.5, 1.5, and 3.0 hours, which are shown in FIG. 6.

Figure 6:
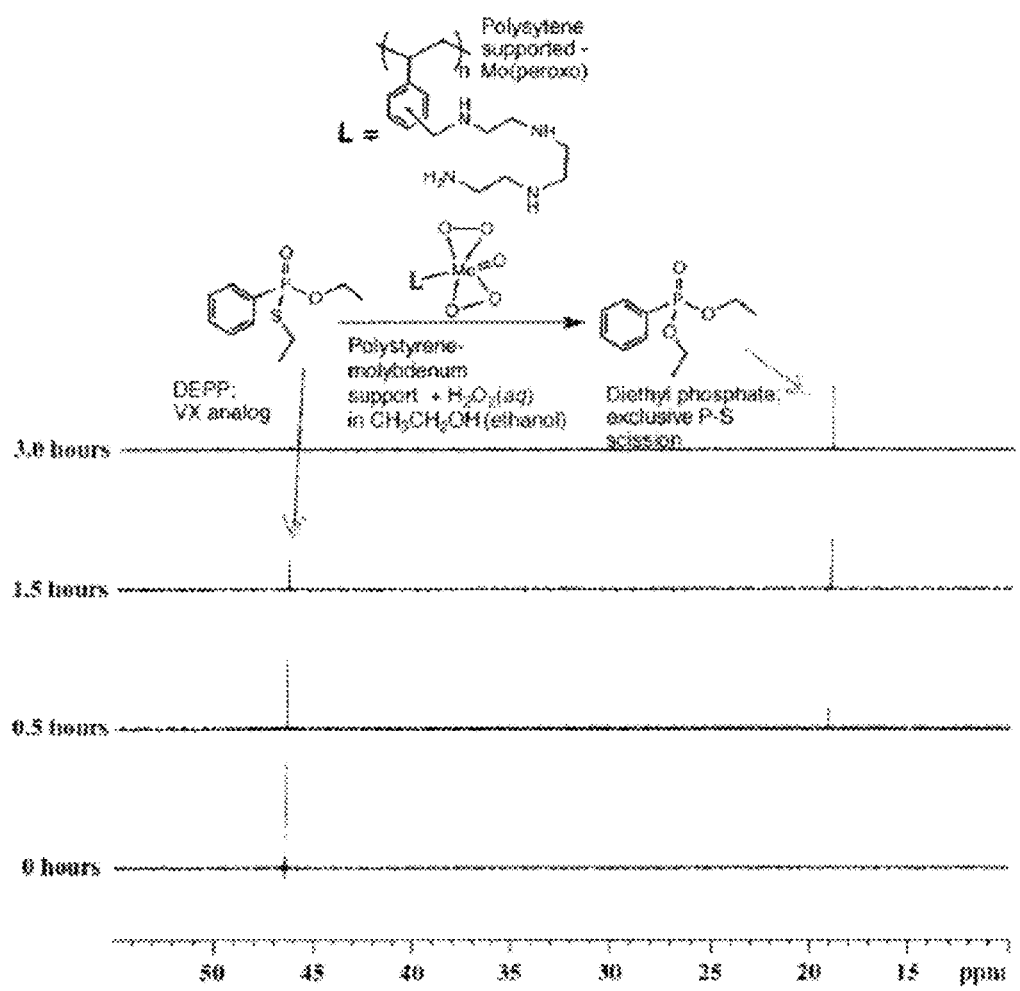
FIG. 6 is a phosphorus-31 NMR spectra of the degradation of O,S-diethylmethylphosphonothioate (DEPP) according to an embodiment of the invention at 0, 0.5, 1.5, and 3.0 hours.

As shown in FIG. 6 there is exclusive formation of only one reaction product. Formation of the reaction product, diethyl phenylphosphonate, is visible as early as 0.5 hours (peak at ~19 ppm) and the peak continues to grow at the 1.5 hours and 3.0 hour measurements. Consistently the peak for DEPP at ~47 ppm is largest at the 0 hours mark and continues to decrease at each measurement indicating the degradation of the phosphate ester and formation of the predominant diethyl phenylphosphonate reaction product. The reaction produce was confirmed with authentic addition. This confirms the selective P—S bond scission. Moreover, the lack of another reaction product peak demonstrates that degradation did not attack the P—O bond, which would have resulted in a toxic phosphonothioate by-product.

The above specification provides a description of the systems and methods for the degradation of phosphate esters. The inventions being thus described, it will be obvious that the same may be varied in many ways. Such variations are not to be regarded as a departure from the spirit and scope of the inventions and all such modifications are intended to be included within the scope of the following claims. Since many embodiments can be made without departing from the spirit and scope of the invention, the invention resides in the claims.

What is claimed is:

1. A system for degrading a phosphate ester comprising:
   a molybdenum(VI) complex comprising one or more monomers of the following formula:

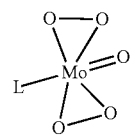

wherein L is a carbon-based support;
   a phosphate ester;
   a peroxygen source; and
   water, a polar solvent, or a combination thereof.

2. The system of claim 1, wherein the carbon-based support comprises a polyacrylate, a polystyrene, or a mesoporous silica.

3. The system of claim 2, wherein the polystyrene comprises

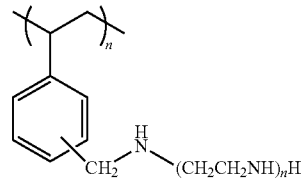

wherein n is between 10 and 10,000.

4. The system of claim 1, further comprising a recovery apparatus, wherein the recovery apparatus contains a phosphorous-containing compound derived from a degraded phosphate ester.

5. The system of claim 4, wherein the phosphorus-containing compound is diethyl phosphite or diethyl phenylphosphonate.

6. The system of claim 1, wherein the system comprises a reaction vessel.

7. The system of claim 6, wherein the reaction vessel comprises an inlet, an outlet, and/or a temperature control wherein the temperature of the system is between about 20° C. and about 45° C.

8. The system of claim 1, wherein the phosphate ester is one or more of

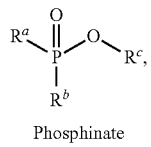

Phosphinate

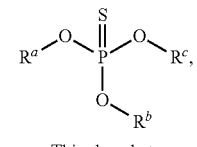

Thiophosphate

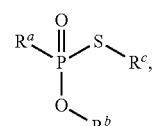

Phosphonothioate

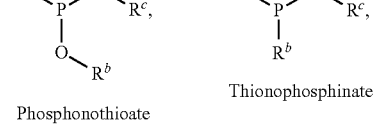

Thionophosphinate

-continued

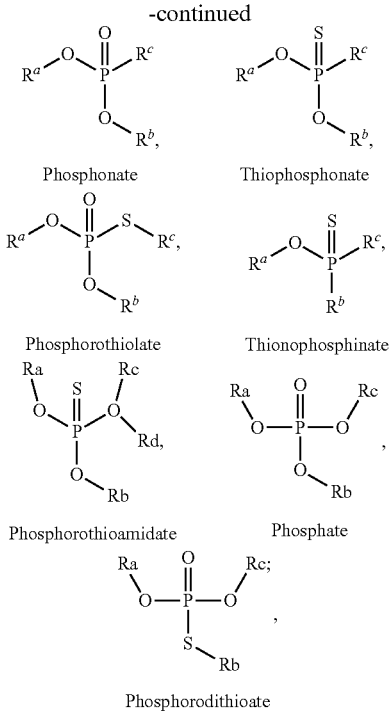

Phosphonate

Thiophosphonate

Phosphorothiolate

Thionophosphinate

Phosphorothioamidate

Phosphate

Phosphorodithioate wherein Ra, Rb, and Rc are selected from the group consisting of hydrogen atoms, halides, R, OR, OCOR, SR, $NR_2$, and $PR_2$; and wherein R is selected from the group consisting of linear, branched, saturated and unsaturated $C_1$-$C_{20}$ alkyl, $C_3$-$C_{20}$ cycloalkyl, $C_6$-$C_{20}$ aryl, $C_7$-$C_{20}$ alkylaryl, $C_7$-$C_{20}$ arylalkyl radicals, optionally containing one heteroatom and multiple heteroatoms belonging to groups 13-17 of the Periodic Table.

9. A method of degrading a phosphate ester comprising:
combining a phosphate ester, a peroxygen source, and a molybdenum(VI) complex comprising one or more monomers of the following formula:

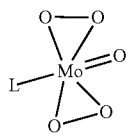

wherein L is a carbon-based support; and
reacting the phosphate ester, the peroxygen source, and the molybdenum(VI) complex.

10. The method of claim 9, wherein the reacting and/or combining steps occur in a medium comprising water, a polar solvent, or a combination thereof.

11. The method of claim 9 wherein the peroxygen source is selected from the group consisting of hydrogen peroxide, t-butyl peroxide, and a mixture thereof.

12. The method of claim 9, wherein the ratio of the peroxygen source to the phosphate ester is at least about 2:1, and wherein the ratio of the peroxygen source to the molybdenum(VI) complex is at least about 2:1.

13. The method of claim 9, wherein the carbon-based support comprises a polyacrylate, a polystyrene, or a mesoporous silica.

14. The method of claim 9, wherein the polystyrene comprises

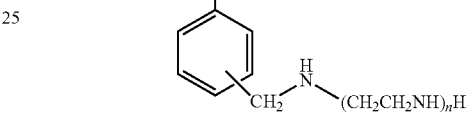

wherein n is between 10 and 10,000.

15. The method of claim 9, wherein the reacting step occurs at a temperature between about 20° C. and about 45° C.

16. The method of claim 9, wherein the molybdenum(VI) complex is prepared by mixing molybdenum(VI) powder with a carbon-support in a liquid medium prior to the combining step.

17. The method of claim 9, wherein the reacting step comprises a selective P—S bond scission.

18. The method of claim 9, further comprising collecting a reaction product, wherein the reaction product comprises diethyl phosphite or diethyl phenylphosphonate.

19. The method of claim 9, wherein the reacting step is performed for a time between about 6 hours and about 10 days.

* * * * *